(12) United States Patent
Liu et al.

(10) Patent No.: US 6,193,961 B1
(45) Date of Patent: Feb. 27, 2001

(54) PERSONAL CARE COMPOSITION CONTAINING A HOMOGENEOUS TERPOLYMER OF AN N-VINYL LACTAM AND A POLYSILOXANE

(75) Inventors: Kou-Chang Liu, Wayne; Jenn S. Shih, Paramus, both of NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/495,129

(22) Filed: Feb. 1, 2000

Related U.S. Application Data

(63) Continuation-in-part of application No. 09/014,464, filed on Jan. 28, 1998, now abandoned.

(51) Int. Cl.$^7$ .......................... A61K 7/075; A61K 31/79
(52) U.S. Cl. ....................... 424/70.12; 424/70.15
(58) Field of Search ............................ 424/70.12, 70.15

(56) References Cited

U.S. PATENT DOCUMENTS 5,480,634 * 1/1996 Hayama et al. .................. 424/70.12
5,609,865 * 3/1997 Liu et al. .......................... 424/78.24

* cited by examiner

*Primary Examiner*—Peter F. Kulkosky
(74) *Attorney, Agent, or Firm*—Marilyn J. Maue; William J. Davis; Walter Katz

(57) ABSTRACT

A homogeneous terpolymer of random monomer distribution containing (a) from abut 32 to about 90% of an N-vinyl lactam, (b) from about 0.5 to about 20% of a mono- or di-functional polysiloxane and (c) from about 5 to about 48% of quaternized or non-quaternized dimethylaminoalkyl-acrylate, methacrylate, acrylamide or methacrylamide combined to form a 100% terpolymer having an excess of vinyl lactam moiety with respect to (c); which terpolymer is useful in a personal care applications, particularly as a hair fixative and conditioner where colorless and clear film forming properties of the terpolymer provides a superior silky, lustrous appearance to the hair without altering hair color or shade, particularly without alteration to dyed or bleached hair.

14 Claims, No Drawings

PERSONAL CARE COMPOSITION CONTAINING A HOMOGENEOUS TERPOLYMER OF AN N-VINYL LACTAM AND A POLYSILOXANE

This application is a continuation-in-part of U.S. application Ser. No. 09/014,464 filed on Jan. 28, 1998, Abandoned.

BACKGROUND OF THE INVENTION

1. Field of the Invention

This invention relates to homogeneous terpolymers of an N-vinyl lactam, and at least one vinyl polysiloxane in predetermined concentrations and in random monomer distribution in the terpolymer structure to more uniformly diffuse the individual properties of each monomer.

2. Description of the Prior Art

Several non-volatile polysiloxane polymers e.g. polyethylene oxide or polypropylene oxide modified types, (Dow Corning DC-1248) have been proposed as hair shampoo additives. Such polysiloxanes can be employed as encapsulating agents for active components as described in U.S. Pat. No. 5,156,914. However, the use of most polysiloxanes in formulations is somewhat limited by their high water insolubility.

Many synthetic polymers containing vinyl lactams are employed in hair and skin care applications of the prior art. Representative of this art are U.S. Pat. Nos. 3,914,403; 3,954,960; 4,039,734, 4,057,533; 4,210,161; 4,223,009, 4,586,518; 4,764,363; 4,834,968; 4,842,850; 4,902,499; 4,906,459; 4,923,694; 4,963,348; 4,983,77; 5,011,895; 5,015,708; 5,126,124; 5,158,762; 5,275,809; 5,502,136; WO 91/15186; WO 91/15185; EPO 412704A2; EPO 0412707A1 and JP 57126409.

Several U.S. patents disclose the use of a N-vinyl lactam, an alkylaminoalkyl (meth)acrylate or (meth)acrylamide as a polymer suitable for use in the pharmaceutical and cosmetic arts, particularly for use in hair spray compositions. These patents are U.S. Pat. Nos. 3,910,862; 4,923,694; 5,045,617; 5,321,110; 5,492,988 and 5,637,296 and of these, only U.S. Pat. Nos. 5,492,988; 5,684,105; 5,609,865 and 5,626,836 disclose a homogeneous polymer structure. However, the homogeneous polymers of the prior art lack the essential third monomer unit of the present invention which provides superior shine and soft, silky appearance to the hair without sacrificing body building and durable film forming properties. Several patents describe the use of insoluble silicones with surfactants in shampoo formulations for removal of excess oils. These patents are PCT 760,132; U.S. Pat. Nos. 4,704,272; 4,741,855; 4,36,837 and 4,788,006. U.S. Pat. No. 5,156,914 describes the encapsulation of silicone oils and gums with surfactant in a polymer matrix for use in a shampoo formulation. However the discrete silicone droplets encapsulated in the polymer are not distributed throughout the polymer and diffusion of monomeric properties as in homogeneous polymers is not achieved. The PCT 760,132 graft polymers fails to obtain uniformity in the beneficial properties of homogeneous polymers.

The homogeneous polymer structure is achieved only by the processes disclosed in U.S. Pat. Nos. 5,609,865; 5,626, 836; 5,492,988 and 5,684,105 whose teachings are incorporated herein by reference. The homogeneous polymerization process generally comprises monitoring the feed rate of the more active monomer species with the rate of consumption of the less active monomer species.

Accordingly, it is an object of this invention to provide a new and colorless terpolymer of homogeneous structure having additional benefits for cosmetic and personal care formulations.

Another object is to provide a polymer having superior hair luster and tone without sacrifice to body building and durable film forming properties for use in a hair fixative composition which terpolymer is quick drying and provides a soft natural appearance.

Another object centers on the ability to adjust the degree of hair hold and conditioning by the choice of certain polyfunctional monomers in the homogeneous terpolymer system.

Still another object is to provide a terpolymer having random distribution of monomer units in the polymer so as to substantially and uniformly distribute the properties of the individual monomers throughout the polymer.

These and other benefits and uses of the present invention will become apparent from the following description and disclosure.

DEFINITIONS

For the purposes of this invention, the term "polymer" is intended to describe the polymer containing three distinct monomer unit species as more particularly defined hereinafter. The terms "acrylamide" and "acrylate" as used alone or in combined form, are intended to include the methacrylamide, methacrylate and visa versa. For example, "dimethylamino ethylmethacrylate" (DMAEMA) is intended to include dimethylamino ethylacrylate, used alone or both in admixture unless otherwise indicated. Similarly, "dimethylamino propylmethacrylamide" (DMAPMA), is intended to include dimethylamino propyl acrylamide, used alone or both in admixture unless otherwise indicated.

A personal care concentrate of the present invention as used for example in a hair spray, hair styling mousse or gel, comprises the present homogeneous terpolymer concentrate diluted in an aqueous, aqueous-alcoholic or alcohol solvent wherein the concentration of the polymer is between about 0.1 and about 10 wt. %, preferably between about 0.5 and about 2 wt. %. Before dilution, the concentrate contains between about 10 and about 70 wt. %, preferably between about 30 and about 55 wt. % terpolymer in aqueous and/or alcoholic solution.

A 50–60% VOC (volatile organic compounds) pump hair spray composition is a solution or suspension of the present homogeneous terpolymer containing from about 1 to about 10% solids, preferably from about 2 to about 5.5% solids, in 60% or less solvent, such as an alcohol, e.g. ethanol, the remainder being water and excipients at the option of the formulator but preferably contains a corrosion inhibitor.

A 50–60% VOC aerosol hair spray of this invention contains between about 1 and about 10% solids, preferably between about 2 and about 4% solids, in a microsuspension of the homogeneous terpolymer, 20% or less alcohol, preferably ethanol, and 35% or less propellant, e.g. dimethyl ether. Generally the composition also contains a neutralizer and other excipients as well as a corrosion inhibitor, e.g. ethoxylated butynediol, a thioester, etc.

SUMMARY OF THE INVENTION

In accordance with this invention there is provided a homogeneous terpolymer of (a) from about 32 to about 90 wt. % of a N-vinyl lactam, (b) from about 5 to about 48 wt. % of dimethylaminoalkyl acrylate or acrylamide and(c) from about 0.5 to about 20 wt. % of a mono- or polyfunctional polysiloxane monomer The N-vinyl pyrrolidone (VP) and/or N-vinyl caprolactam (VCL) components may optionally contain one or two $C_1$ to $C_4$ alkyl groups substituted on their respective heterocyclic rings.

The terpolymers of this invention have a weight average molecular weight of from about 10,000 to about 5,000,000, a Hack turbidity preferably less than 5 and contain an excess amount of the vinyl lactam units.

DETAILED DESCRIPTION OF THE INVENTION

Within the broad definition of the present polymer, the preferred homogeneous polymer of this invention contains, as the first component, from about 40 to about 85 wt. % of the N-vinyl lactam moiety, most preferably from 60 to 80 wt. %. The N-vinyl lactam component comprises from 0 to 100% VP, from 0 to 100% VCL or mixtures of these monomers; these monomers being most preferably unsubstituted. When a mixture of VP and VCL is employed, a mole ratio of between about 5:1 and about 1:5 is preferred.

The second quaternized or non-quaternized amino component of the polymer which is employed in a minor amount with respect to the vinyl lactam, is preferably present at a concentration of from about 10 to about 30 wt. % and is an acrylate or acrylamide defined by the formula:

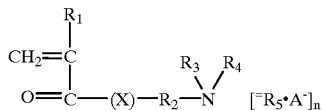

wherein $R_1$ is hydrogen or methyl; $R_2$ is $C_2$ to $C_{20}$ alkylene; n has a value of 0 or 1;

X is oxygen or

$R_6$, $R_3$ and $R_4$ are each independently hydrogen or $C_1$ to $C_4$ alkyl; $R_5$ is $C_1$ to $C_5$ alkyl and A is any anion including a halide, sulfate, sulfonate, phosphate, tosylate etc. As the second (b) component, mixtures of quaternized and non-quaternized compounds are included as well as mixtures of compounds designated by X such as mixtures of aminoalkyl acrylate and aminoalkylacrylamide in a quaternized or non-quaternized state. Particularly preferred species of (b) are the quaternized and non-quaternized dimethylamino propyl methacrylate, dimethylamino propylacrylate, dimethylamino ethylacrylate, 3-methyl acrylamidopropyl trimethyl ammonium chloride (MAPTAC), 3-methylacrylamido propyl dimethylethyl tosylate and dimethylamino propyl methacrylamide (DMAPMA).

The polysiloxane component (c) is preferably employed at a concentration of from 1 to 15 wt. % for the monofunctional polysiloxane (MVPS) and from about 0.5 to about 10 wt. % for the difunctional polysiloxane (DVPS). Most preferably a concentration of from 2 to 10% monofunctional or 1 to 6% difunctional polysiloxane is employed. The siloxane monomer is broadly described by the formula:

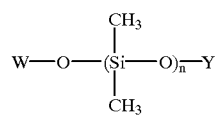

wherein n has a value of from 1 to 100;
W is vinyl dimethyl silyl,

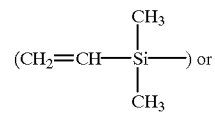

methacryloxyalkyl dimethyl silyl,

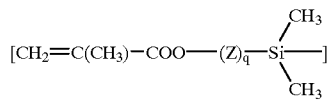

wherein q has a value of from 1 to 50, preferably 2 to 10, Y=W or Y is phenyl or $CH_3(CH_2)_p$ where p has a value from 0 to 6 and Z is methylene or $C_2$ to $C_4$ alkylene oxide. Examples of the silyl monomers include mono- or di-methacryloxy propyl terminated polydimethyl siloxane, mono- or di-acryloxy propyl terminated polydimethylsiloxane and di-vinyl terminated polydimethylsiloxane. Mixtures of vinyl polysiloxane monomers are also included in this invention as the third component of the terpolymer. The preferred species of the vinyl polysiloxanes are those wherein alkyl is methyl or ethyl and include vnyl poly (dimethylsiloxane); divinyl poly(dimethylsiloxane; vinyl poly(dimethylsiloxane/methyl vinylsiloxane); vnyl poly (dimethylsiloxane/methylphenyl-siloxane); polyalkylene oxide modified siloxanes are also suitable for monomers of the present invention as well as mixed aliphatic/aromatic types supplied by General Electric (VISCASIL series) and Dow Corning (200 series) having Brookfield viscosities between about 5–600,000 cps preferably 300–1,000 cps. Other suitable polysiloxanes are polymerizable species disclosed in U.S. Pat. Nos. 4,788,006; 4,741,855; 4,704,272 and 4,364,837.

The polysiloxane moiety in the present homogeneous terpolymer reinforces body building and luster to hair while increasing combability. The polyfunctional siloxane introduces a degree of crosslinking in the terpolymer which further promotes hair body building properties and produces a firmer hold.

In the present invention, the high water insolubility of the polysiloxane component is overcome by the homogeneous structure of the terpolymer where monomer moieties are randomly distributed as opposed to blocks of polysiloxane moieties which concentrate hydrophobicity.

A further benefit of the siloxane moiety in the present homogeneous terpolymer is that the silky texture imparted to the hair is not accompanied with the commonly associated attraction of static electricity which is responsible for "fly away", unmanageable hair. Incorporation of the siloxane moiety in the homogeneous polymer reinforces body building, luster and soft feel to hair while increasing combability. The polyfunctional siloxane introduces a degree of crosslinking in the polymer which further promotes hair body building properties and produces a firmer stronger hold.

The present terpolymer is generally prepared according to the homogeneous polymerization process disclosed in U.S. Pat. Nos. 5,492,988; 5,609,865; 5,684,105 and 5,626,836; the teachings of which is incorporated herein by reference. In summary, the process involves precharging the monomer having the lowest reactivity and initiator prior to the charge of major amounts of the remaining monomers having higher reactivity and controlling the gradual feed rate of the more reactive monomer species so that the relative concentrations of all monomer species remain constant throughout the polymerization reaction and the product, at completion of the polymerization, contains less than 0.1% unreacted lactam monomer.

Suitable initiators for the homogeneous polymerization reaction are the conventional free radical types which include organic and inorganic compounds such as hydrogen peroxide, lauryl peroxide, t-butylperoxy pivalate (LUPERSOL® 11); t-amylperoxy pivalate (LUPERSOL® 554); dimethyl 2,5-di(t-butylperoxy) hexane (LUPERSOL® 101); azobis(butyronitrile); azobis(methylnitrile); azobis (diisobutyronitrile); azobis(isovaleronitrile); azobis (cyclohexanecarbonitrile) etc.

The solution polymerization is carried out at a temperature of between about 50° and about 90° C., preferably between about 60° and about 80° C. for a period of from about 4 to about 100 hours, more conveniently from about 6 to about 30 hours or until the polymerization is completed by indication of the above trace amounts of residual monomer.

To obtain the present polymer having a homogeneous structure it is critical that part or all of the least reactive monomer be precharged into a reactor and that at least a major portion of the more reactive remaining monomers, be then introduced incrementally or continuously into the precharged reactor at such rates that allow the ratio of the relative concentrations of all monomers to remain constant throughout the reaction so that all monomers can react to form a substantially homogeneous polymer in a desired compositional ratio. Consequently, a substantially homogeneous polymer of this invention is obtained whose composition approaches the nominal monomer ratio of the desired polymer composition and whose structure contains at least three individual monomeric moieties which are distributed substantially uniformly in a homogeneous chain along the acrylate/siloxane backbone of the polymer.

The precharge in the process of the invention may include a portion of the more active component monomers, generally in an amount of up to about 30% of the total amount of second and third comonomers required for a predetermined terpolymer composition without affecting the homogeneous polymerization process.

The schedule of addition to accomplish the desired matched rate of reaction is described in following Examples.

EXAMPLE 1

Preparation of a Homogeneous Terpolymer of 74% VP, 20% DMAPMA and 6% Witico Y-14225

Initially, vinylpyrrolidone (VP), dimethylaminopropyl-methacrylamide (DMAPMA) and Witico Y-14225, an acrylated siloxane polyalkylene oxide copolymer, and ethanol were charged into a two liter resin pot equipped with a gas inlet, a liquid inlet, a thermometer, a condenser and a mechanical stirrer. The solution was gradually heated to 78° C. and a stream of nitrogen introduced which bubbled through the solution during the reaction to remove oxygen from the system. The remaining amounts of the monomers were then added to the solution according to the time shown in Table I, so that the relative concentrations of the component monomers remained practically constant throughout the reaction.

An ethanol solution of 2,2'-azobis(2-methylbutane-nitrile) (Vazo-67) initiator was added to the reaction pot as soon as the scheduled monomer feedings started. A total of 4.4 g of the initiator solution was added in portion over 5.5 hours. The solution was held for an additional 10 hours at 78° C. to yield an ethanol solution of compositionally homogeneous copolymer of VP/DMAPMA/Y-14225.

TABLE I

| Time (min) | VP (g) | DMAPMA (ml) | Y-14225 Si (ml) | EtOH (ml) | Total (g) |
|---|---|---|---|---|---|
| 0 | 444 | 12.77 | 3.5 | 1000.13 | 1244.71 |
| 0–30 |  | 23.98 | 6.57 | 30.55 | 1298 |
| 30–60 |  | 23.43 | 6.42 | 29.85 | 1350.07 |
| 60–90 |  | 19.2 | 5.26 | 24.46 | 1392.74 |
| 90–120 |  | 15.08 | 4.13 | 19.21 | 1426.25 |
| 120–150 |  | 11.03 | 3.02 | 14.05 | 1450.76 |
| 150–180 |  | 7.98 | 2.19 | 10.17 | 1468.5 |
| 180–210 |  | 5.67 | 1.55 | 7.22 | 1481.03 |
| 210–240 |  | 3.95 | 1.08 | 5.03 | 1489.86 |
| 240–270 |  | 2.71 | 0.74 | 3.45 | 1495.88 |
| 270–300 |  | 1.86 | 0.51 | 2.38 | 1500.02 |
| Total (g) | 444 | 120 | 36 | 900 | 1500 |

EXAMPLE 2

Preparation of a Homogeneous Terpolymer of 83% VP, 15% MAPTAC and 2% Huls PS441

Initially, vinylpyrrolidone (VP), 3-trimethyl-ammonium propylmethacrylamide chloride (MAPTAC), Huls PS-441, a vinyldimethyl terminated polydimethylsiloxane (viscosity= 100 cps), and methanol are charged into a two liter resin pot equipped with a gas inlet, a liquid inlet, a thermometer, a condenser and a mechanical stirrer. The solution is gradually heated to 75° C. and a stream of nitrogen introduced which bubbled through the solution during the reaction to remove oxygen from the system. The remaining amounts of the monomers are then added to the solution according to the time shown in Table II, so that the relative concentrations of the component monomers remained practically constant throughout the reaction.

A methanol solution of 2,2'-azobis(2-methylbutane-nitrile) (Vazo-67) initiator is added to the reaction pot as soon as the scheduled monomer feedings started. A total of 4.4 g of the initiator solution is added in portion over 5.5 hours. The solution is held for an additional 12 hours at 75° C. to yield a methanol solution of compositionally homogeneous copolymer of VP/MAPTAC/PS-441.

TABLE II

| Time (min) | VP (g) | MAPTAC (ml) | PS-441 Si (ml) | MeOH (ml) | Total (g) |
|---|---|---|---|---|---|
| 0 | 581 | 9.97 | 14 | 750.56 | 1356.06 |
| 0–30 |  | 39.55 |  |  | 1397.71 |
| 30–60 |  | 38.64 |  |  | 1438.4 |
| 60–90 |  | 31.66 |  |  | 1471.74 |
| 90–120 |  | 24.87 |  |  | 1497.93 |
| 120–150 |  | 18.19 |  |  | 1517.08 |
| 150–180 |  | 13.16 |  |  | 1530.94 |
| 180–210 |  | 9.35 |  |  | 1540.79 |

TABLE II-continued

| Time (min) | VP (g) | MAPTAC (ml) | PS-441 Si (ml) | MeOH (ml) | Total (g) |
|---|---|---|---|---|---|
| 210–240 | | 6.51 | | | 1547.65 |
| 240–270 | | 4.47 | | | 1552.36 |
| 270–300 | | 3.08 | | | 1555.6 |
| Total (g) | 581 | 210 | 14 | 750.56 | 1555.56 |

MAPTAC is 50% aqueous

EXAMPLE 3

Preparation of a Homogeneous Terpolymer of 65% VCL, 30% DMAPMA-50% DES quat and 5% Huls PS-583

Initially, vinylpyrrolidone (VP), 50% diethylsulfate quaternized dimethylaminopropylmethacrylamide (DMAPMA-50% DES quat) and Huls PS-583, a polydimethyl siloxane methacryloxypropyl terminated, and ethanol are charged into a two liter resin pot equipped with a gas inlet, a liquid inlet, a thermometer, a condenser and a mechanical stirrer. The solution is gradually heated to 78° C. and a stream of nitrogen introduced which bubbled through the solution during the reaction to remove oxygen from the system. The remaining amounts of the monomers are then added to the solution according to the time shown in Table III, so that the relative concentrations of the component monomers remained practically constant throughout the reaction.

An ethanol solution of 2,2'-azobis(2-methylbutane-nitrile) (Vazo-67) initiator is added to the reaction pot as soon as the scheduled monomer feedings started. A total of 4.4 g of the initiator solution is added in portion over 5.5 hours. The solution is held for an additional 10 hours at 78° C. to yield an ethanol solution of compositionally homogeneous copolymer of VP/DMAPMA-50% DES quat/PS-583.

TABLE III

| Time (min) | VCL (g) | DMAPMA (ml) | PS-583 Si (ml) | EtOH (ml) | Total (g) |
|---|---|---|---|---|---|
| 0 | 341.25 | 7.9 | 1.31 | 1051.43 | 1175.81 |
| 0–30 | | 31.32 | 5.21 | 39.78 | 1243.47 |
| 30–60 | | 30.6 | 5.09 | 38.87 | 1309.58 |
| 60–90 | | 25.08 | 4.17 | 31.85 | 1363.76 |
| 90–120 | | 19.7 | 3.27 | 25.02 | 1406.31 |
| 120–150 | | 14.41 | 2.39 | 18.3 | 1437.43 |
| 150–180 | | 10.42 | 1.73 | 13.24 | 1459.94 |
| 180–210 | | 7.4 | 1.23 | 9.4 | 1475.93 |
| 210–240 | | 5.16 | 0.86 | 6.55 | 1487.08 |
| 240–270 | | 3.54 | 0.59 | 4.5 | 1494.73 |
| 270–300 | | 2.43 | 0.4 | 3.09 | 1499.98 |
| Total (g) | 341.25 | 157.5 | 26.25 | 975 | 1500 |

EXAMPLE 4

Preparation of a Homogeneous Terpolymer of 35% VP, 45% VCL, 15% DMAEMA and 5% Huls PS-442

Initially, vinylpyrrolidone (VP), vinyl caprolactam (VCL), DMAEMA (2-dimethylaminoethyl methacrylate), and Huls PS-442, a vinyldimethyl terminated polydimethylsiloxane (viscosity=500 cps), and ethanol are charged into a two liter resin pot equipped with a gas inlet, a liquid inlet, a thermometer, a condenser and a mechanical stirrer. The solution is gradually heated to 75° C. and a stream of nitrogen introduced which bubbled through the solution during the reaction to remove oxygen from the system. The remaining amounts of the monomers are then added to the solution according to the time shown in Table IV, so that the relative concentrations of the component monomers remained practically constant throughout the reaction.

Luperson-11 initiator (t-butylperoxypivalate) is added to the reaction pot as soon as the scheduled monomer feedings started. A total of 1.0 g of the initiator solution is added in portion over 6 hours. The solution is held for an additional 10 hours at 75° C. to yield an ethanol solution of compositionally homogeneous copolymer of VP/VCL/DMAEMA/PS-442.

TABLE IV

| Time (min) | VCL (g) | VP (ml) | DMAEMA (ml) | PS442 Si (g) | EtOH (ml) | Total (g) |
|---|---|---|---|---|---|---|
| 0 | 202.5 | 76.17 | 3.62 | 22.5 | 1193.59 | 1244.56 |
| 0–30 | | 43.94 | 14.35 | | 58.29 | 1349.4 |
| 30–60 | | 20.1 | 14.01 | | 34.11 | 1410.15 |
| 60–90 | | 8.13 | 11.48 | | 19.61 | 1444.71 |
| 90–120 | | 3.1 | 9.02 | | 12.12 | 1465.86 |
| 120–150 | | | 6.6 | | 6.6 | 1477.2 |
| 150–180 | | | 4.77 | | 4.77 | 1485.39 |
| 180–210 | | | 3.39 | | 3.39 | 1491.21 |
| 210–240 | | | 2.36 | | 2.36 | 1495.26 |
| 240–270 | | | 1.62 | | 1.62 | 1498.04 |
| 270–300 | | | 1.11 | | 1.11 | 1499.95 |
| Total (g) | 202.5 | 157.5 | 67.5 | 22.5 | 1050 | 1500 |

EXAMPLE 5

Preparation of a Homogeneous Terpolymer of 70% VP, 20% DMAPMA and 10% Huls PS-560

Initially, vinylpyrrolidone (VP), dimethylaminopropylmethacrylamide (DMAPMA) and Huls PS-560, a polydimethyl siloxane monomethacryloxypropyl terminated, and ethanol are charged into a two liter resin pot equipped with a gas inlet, a liquid inlet, a thermometer, a condenser and a mechanical stirrer. The solution is gradually heated to 78° C. and a stream of nitrogen introduced which bubbled through the solution during the reaction to remove oxygen from the system. The remaining amounts of the monomers are then added to the solution according to the time shown in Table V, so that the relative concentrations of the component monomers remained practically constant throughout the reaction.

An ethanol solution of 2,2'-azobis(2-methylbutane-nitrile) (Vazo-67) initiator is added to the reaction pot as soon as the scheduled monomer feedings started. A total of 4.4 g of the initiator solution is added in portion over 5.5 hours. The solution is held for an additional 10 hours at 78° C. to yield an ethanol solution of compositionally homogeneous copolymer of VP/DMAPMA/PS-560.

TABLE V

| Time (min) | VP (g) | DMAPMA (ml) | PS-560 Si (ml) | EtOH (ml) | Total (g) |
|---|---|---|---|---|---|
| 0 | 420 | 6.38 | 3 | 968.22 | 1189.05 |
| 0–30 | | 25.31 | 11.9 | 37.21 | 1253.95 |
| 30–60 | | 24.73 | 11.62 | 36.36 | 1317.36 |
| 60–90 | | 20.27 | 9.53 | 29.79 | 1369.33 |
| 90–120 | | 15.92 | 7.48 | 23.4 | 1410.14 |

TABLE V-continued

| Time (min) | VP (g) | DMAPMA (ml) | PS-560 Si (ml) | EtOH (ml) | Total (g) |
|---|---|---|---|---|---|
| 120–150 |  | 11.64 | 5.47 | 17.12 | 1439.99 |
| 150–180 |  | 8.42 | 3.96 | 12.38 | 1461.58 |
| 180–210 |  | 5.98 | 2.81 | 8.79 | 1476.91 |
| 210–240 |  | 4.17 | 1.96 | 6.13 | 1487.6 |
| 240–270 |  | 2.86 | 1.35 | 4.21 | 1494.94 |
| 270–300 |  | 1.97 | 0.92 | 2.89 | 1499.98 |
| Total (g) | 420 | 120 | 60 | 900 | 1500 |

Representative applications of the present polymer are the following:

HAIR CARE COMPOSITIONS

In a water-based, hair styling and conditioning composition, the homogeneous polymer of the invention comprises about 0.2–20%, preferably 1–10%, and, most preferably, about 2–8%, by weight of the hair care product, the rest being water, and, optionally including an organic solvent such as ethanol, and/or other acceptable excipient components such as corrosion inhibitors, surface active agents, viscosity modifiers, dyes, chelating agents, distributing aids, pearlescent aids, opacifiers, perfumes, fatty alcohols, pH adjusting agents, and the like.

The homogeneous polymer of the invention also finds particular utility in multifunctional hair care products such as water-based, rinse-off hair styling and conditioning products, and in leave-on hair care products such as a mousse, and may be included as a concentrate, or as a gel, and applied as a self-actuated pump hair spray, or in an aerosol product with a propellant. Various actuator and packaging devices known in the art may be used therewith.

PROCEDURE FOR PREPARING HAIR SPRAY COMPOSITIONS OF INVENTION

A. Pump Spray

The pump hair spray compositions of the invention were prepared by first dissolving the homogeneous polymer resin in ethanol and adding the requisite amount of water. The composition then was packaged into a high density polyethylene bottle fitted with a suitable pump actuator, e.g. a pump sprayer (160 ml) with 0.018×0.010 inch deep actuator (SEAQUIST EUROMIST II).

B. Aerosol Spray

The aerosol hair spray resin compositions of the invention were prepared from 65% by weight of the hair spray concentrate, a vapor phase inhibitor, a liquid phase inhibitor, adjuvants where needed, and 35% by weight of a propellant, e.g. dimethyl ether.

EXAMPLES 6–9

The following hair spray compositions of the invention were prepared in a stainless steel mixing vessel and mixed at ambient temperature for 20 minutes with a turbine agitator.

TABLE VI

HAIR SPRAY COMPOSITIONS

| Example No. | 6 | 7 | 8 | 9 |
|---|---|---|---|---|
| Component | Weight % | | | |
| Homogeneous polymer of Ex. 1 (45% active in ethanol) | 8.90 | 6.67 | 8.90 | 6.67 |
| Water | 41.00 | 42.00 | 40.50 | 41.50 |
| Excipients |  |  | 0.50 | 0.50 |
| Propellant |  |  | 35.00 | 35.00 |
| Ethanol | 50.10 | 51.33 | 15.10 | 16.33 |
|  | 100.00 | 100.00 | 100.00 | 100.00 |

COMPARATIVE EXAMPLE 10

The following comparative hair spray composition was prepared in the manner set forth above.

TABLE VII

| Component | Weight % |
|---|---|
| Non-Homogeneous polymer of Ex. 1 (45% active in ethanol) | 8.90 |
| Water | 41.00 |
| Ethanol | 50.10 |

HAIR SPRAY PROPERTIES
INVENTION VS. COMPARATIVE EXAMPLE

|  | Homogeneous Composition (Ex. 6) | Non-Homogeneous Composition (Ex. 10) |
|---|---|---|
| Turbidity (HACH) | 0.6 | 40.1 |
| HHCR (90 min) | 88.6 | 84.2 |
| (4 hr.) | 76.6 | 75.3 |
| Particle size, DAV [V, 0.5] | 85.3 | 95.3 |
| Stiffness | 8.3 | 6.7 |
| Curl snap | 9.0 | 6.7 |
| Curl memory | 7.7 | 4.0 |

While the invention has been described with particular reference to certain embodiments thereof, it will be understood that many changes and modifications within the scope of the foregoing disclosure may be made which are within the sill of the art. Accordingly, it is intended to be bound only by the following claims, in which:

What is claimed is:

1. A substantially clear, homogeneous polymer as an active fixative for hair spray having a high curl memory and consisting essentially of (a) from about 32 to about 90 wt. % of a N-vinyl lactam, (b) from about 5 to about 48 wt. % of a quaternized and/or a non/quaternized dialkylaminoalkyl-(meth) acrylate and/or -(meth)acrylamide, and (c) from about 0.5 to about 20 wt. % of a mono- or di-functional polysiloxane; all monomers combined in 100% composition wherein the polymer contains a major amount of vinyl lactam units with respect to (b).

2. The homogeneous polymer of claim 1 containing from about 40 to about 85 wt. % of (a), from about 10 to about 30 wt. % of (b) and from about 1 to about 15 wt. % of monofunctional polysiloxane.

3. The homogeneous polymer of claim 1 containing from about 2 to about 10 wt. % of monofunctional polysiloxane.

4. The homogeneous polymer of claim 1 containing from about 40 to about 85 wt. % of (a), from about 10 to about 30 wt. % of (b) and from about 0.5 to about 10 wt. % of difunctional polysiloxane.

5. The homogeneous polymer of claim 3 containing from about 1 to about 6 wt. % of difunctional polysiloxane.

6. The homogeneous polymer of claim 1 wherein said polysiloxane has the formula:

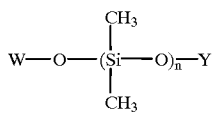

wherein n has a value of from 1 to 100;

W is vinyl dimethyl silyl,

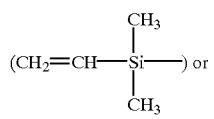

methacryloxyalkyl dimethyl silyl,

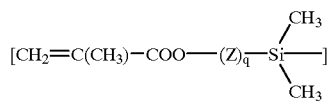

wherein q has a value of from 1 to 50, preferably 2 to 10, Y=W or Y is phenyl or $CH_3(CH_2)_p$ where p has a value from 0 to 6 and Z is methylene or $C_2$ to $C_4$ alkylene oxide.

7. A concentrate of the homogeneous polymer of claim 1 in an aqueous and/or alcoholic medium wherein the concentration of the polymer is between about 10 and about 70 wt. %.

8. The concentrate of claim 7 wherein the concentration of the polymer is between about 30 and about 55 wt. %.

9. A 50–60% VOC pump hair spray fixative composition containing from about 1 to about 10% homogeneous polymer of any one of claims 3 and 4 in less than 65% $C_1$ to $C_4$ alkanol and from about 25 to about 95 wt. % water.

10. A 50–60% VOC aerosol spray composition comprising from about 1 to about 10 wt. % homogeneous polymer of any one of claims 1, 2, 3 and 4 in 20% or less alcohol and 35% or less propellant.

11. The aerosol spray of claim 10 wherein said polymer concentration is between about 2 and about 4 wt. %, the alcohol is ethanol and the propellant is dimethyl ether.

12. A hair mousse or styling gel containing between about 0.1 and about 10 wt. % of the polymer of claim 1.

13. A hair mousse or styling gel containing between about 0.1 and about 10 wt. % of the polymer of claim 2.

14. A hair mousse or styling gel containing between about 0.1 and about 10 wt. % of the polymer of claim 4.

* * * * *